United States Patent
Blaauw et al.

(10) Patent No.: US 7,005,547 B2
(45) Date of Patent: Feb. 28, 2006

(54) PROCESS FOR THE PREPARATION OF CYCLOHEXANONE OXIME

(75) Inventors: Marc Blaauw, Maastricht (NL); Antonius Jacobus Franciscus Simons, Geleen (NL); Henk Oevering, Elsloo (NL)

(73) Assignee: DSM IP Assets B.V., Heerlen (NL)

( * ) Notice: Subject to any disclaimer, the term of this patent is extended or adjusted under 35 U.S.C. 154(b) by 148 days.

(21) Appl. No.: 10/297,308

(22) PCT Filed: May 31, 2001

(86) PCT No.: PCT/NL01/00429

§ 371 (c)(1),
(2), (4) Date: Jan. 9, 2004

(87) PCT Pub. No.: WO01/94298

PCT Pub. Date: Dec. 13, 2001

(65) Prior Publication Data

US 2004/0116745 A1 Jun. 17, 2004

(30) Foreign Application Priority Data

Jun. 5, 2000 (EP) .................................. 00201965

(51) Int. Cl.
*C07C 251/44* (2006.01)
(52) U.S. Cl. ..................................................... 564/259
(58) Field of Classification Search ................. 564/259
See application file for complete search history.

(56) References Cited

U.S. PATENT DOCUMENTS

| 3,862,230 A | * | 1/1975 | De Rooij et al. ........... 564/259 |
| 3,997,607 A | | 12/1976 | de Rooij |
| 4,328,198 A | | 5/1982 | van de Moesdijk |
| 4,994,613 A | * | 2/1991 | Fruchey ...................... 564/259 |

FOREIGN PATENT DOCUMENTS

GB 1138750 1/1969

* cited by examiner

*Primary Examiner*—Brian Davis
(74) *Attorney, Agent, or Firm*—Mayer Brown Rowe & Maw LLP

(57) ABSTRACT

The invention relates to a process for the production of cyclohexanone oxime in which a phosphate-containing aqueous reaction medium is cycled from a hydroxylammonium synthesis zone to a cyclohexanone oxime synthesis zone and back to the hydroxylammonium synthesis zone, in which hydroxylammonium synthesis zone hydroxylammonium is formed by catalytic reduction of nitrate with hydrogen, and in which cyclohexanone oxime synthesis zone hydroxylammonium is reacted with cyclohexanone to form cyclohexanone oxime, the cyclohexanone and an organic solvent being fed into the cyclohexanone oxime synthesis zone, an organic medium comprising the organic solvent and cyclohexanone oxime being withdrawn from the cyclohexanone oxime synthesis zone, characterized in that the ratio $f_h/f_c<1.00$ wherein $f_h$ represents the molar quantity of hydroxylammonium fed to the cyclohexanone oxime synthesis zone per unit of time (in mol/s), and $f_c$ represents the molar quantity of cyclohexanone fed to the cyclohexanone oxime synthesis zone per unit of time (in mol/s).

13 Claims, 1 Drawing Sheet

PROCESS FOR THE PREPARATION OF CYCLOHEXANONE OXIME

CROSS REFERENCE TO RELATED APPLICATIONS

This application is the National Phase of International Application PCT/NL01/00429 filed May 31, 2001 which designated the U.S., and which further claims priority to European application No. 00201965.1, filed Jun. 5, 2000, both of which are hereby incorporated in their entirety by reference.

The present invention relates to a process for the production of cyclohexanone oxime in which a phosphate-containing aqueous reaction medium is cycled from a hydroxylammonium synthesis zone to a cyclohexanone oxime synthesis zone and back to the hydroxylammonium synthesis zone, in which hydroxylammonium synthesis zone hydroxylammonium is formed by catalytic reduction of nitrate with hydrogen, and in which cyclohexanone oxime synthesis zone hydroxylammonium is reacted with cyclohexanone to form cyclohexanone oxime, the cyclohexanone and an organic solvent being fed into the cyclohexanone oxime synthesis zone, an organic medium comprising the organic solvent and cyclohexanone oxime being withdrawn from the cyclohexanone oxime synthesis zone.

Oximes can be produced in a process in which a buffered, aqueous reaction medium containing buffer acids or acidic salts, for example phosphate buffers, and buffer salts derived from these acids, is continuously recycled between a hydroxylammonium synthesis zone in which nitrate ions are catalytically reduced with molecular hydrogen to hydroxylammonium, and an oximation zone where a ketone, e.g. cyclohexanone, is converted to an oxime. Before the aqueous reaction medium is passed into the hydroxylammonium synthesis zone, it may be enriched with the required nitrate ions by addition of nitric acid or by absorption of nitrous gases in the aqueous reaction medium in which instance nitric acid is formed in situ. After having been enriched in hydroxylammonium in the hydroxylammonium synthesis zone, the aqueous reaction medium is then passed to the oxime synthesis zone, where the hydroxylammonium reacts with a ketone, e.g., cyclohexanone, forming the corresponding oxime. The oxime can then be separated from the aqueous reaction medium which is recycled to the hydroxylammonium synthesis zone.

The net chemical reactions occurring during the process can be represented by the following equations:
1) Preparation of the hydroxylammonium:

$$2H_3PO_4 + NO_3^- + 3H_2 \rightarrow NH_3OH^+ + 2H_2PO_4^- + 2H_2O$$

2) Preparation of the oxime

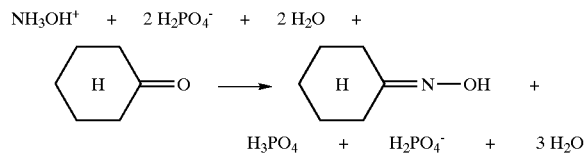

3) Supply of $HNO_3$ to make up the depletion of the source of nitrate ions after removal of the oxime formed

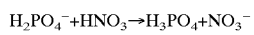

The catalyst used in the reduction of the nitrate ions is generally palladium and/or platinum on a carrier material of carbon or alumina, the carrier material being loaded with from 1 to 25% wt. of palladium and/or platinum. The activity of the catalyst is adversely affected by the presence of organic contaminants, such as the ketone and oxime, in the recycled stream.

A number of techniques have been developed to address this problem of the recycled stream containing high amounts of contaminants that poison the catalyst. U.S. Pat. No. 3,940,442 describes that poisoning of the catalyst is prevented by heating the aqueous reaction medium being recycled from the cyclohexanone oxime synthesis zone to the hydroxylammonium synthesis zone to an elevated temperature in the range of 50° C. to 106° C. GB-A-1,283,894 and U.S. Pat. No. 3,997,607 describe that heat treating the aqueous reaction medium in the presence of nitrous acid, respectively nitrous gases reduce the extent of catalyst poisoning.

It has now been found that a decreased molar ratio of (hydroxylammonium fed to the cyclohexanone oxime synthesis zone per unit of time)/(cyclohexanone fed to the cyclohexanone oxime synthesis zone per unit of time) results in a decrease of the concentration of the organic contaminants in the aqueous reaction medium which is recycled from the cyclohexanone oxime synthesis zone to the hydroxylammonium synthesis zone. Therefore, the invention provides a process for the production of cyclohexanone oxime in which a phosphate-containing aqueous reaction medium is cycled from a hydroxylammonium synthesis zone to a cyclohexanone oxime synthesis zone and back to the hydroxylammonium synthesis zone, in which hydroxylammonium synthesis zone hydroxylammonium is formed by catalytic reduction of nitrate with hydrogen, and in which cyclohexanone oxime synthesis zone hydroxylammonium is reacted with cyclohexanone to form cyclohexanone oxime, the cyclohexanone and an organic solvent being fed into the cyclohexanone oxime synthesis zone, an organic medium comprising the organic solvent and cyclohexanone oxime being withdrawn from the cyclohexanone oxime synthesis zone, characterized in that the ratio $f_h/f_c < 1.00$ wherein $f_h$ represents the molar quantity of hydroxylammonium fed to the cyclohexanone oxime synthesis zone per unit of time (in mol per unit of time), and $f_c$ represents the molar quantity of cyclohexanone fed to the cyclohexanone oxime synthesis zone per unit of time (in mol per unit of time). The invention also provides a process for the production of cyclohexanone oxime in which (i) an aqueous reaction medium containing hydroxylammonium, phosphate and nitrate, (ii) cyclohexanone and (iii) an organic solvent are fed into a cyclohexanone oxime synthesis zone, in which hydroxylammonium is reacted with cyclohexanone to form cyclohexanone oxime, an organic medium comprising the organic solvent and cyclohexanone oxime being withdrawn from the cyclohexanone oxime synthesis zone, characterized in that characterized in that the ratio $f_h/f_c < 1.00$.

Using the process according to the invention, it is possible to decrease the amount of organic contaminants which poison the catalyst, in particular residual cyclohexanone and/or cyclohexanone oxime, entering the hydroxylammonium synthesis zone under further equal circumstances. According to the invention it is also possible to omit steps for the removal of organic contaminants or to lessen the extent to which such steps are carried out, for instance by using smaller equipment, the ratio $f_h/f_c < 1.00$ avoiding or mitigating an increase of the amount of organic contaminants entering the hydroxylammonium synthesis zone. According to the invention, it is also possible to increase the concentration cyclohexanone oxime in the organic medium exiting the cyclohexanone oxime synthesis zone, the ratio $f_h/f_c<1.00$ avoiding or mitigating an increase of the amount of organic contaminants entering the hydroxylammonium synthesis zone.

It is noted that GB-A-1,138,750 describes a process for the production of cyclohexanone oxime in which an aqueous reaction medium containing phosphate and hydroxylammonium obtained in a hydroxylammonium synthesis zone is cycled to a cyclohexanone oxime synthesis zone together with cyclohexanone and toluene. In the known process, the ratio $f_h/f_c$ is equal to 1.00. It is not disclosed that decreasing said ratio results in a decrease of the concentration of organic contaminants in the aqueous reaction medium which is recycled from the cyclohexanone oxime synthesis zone to the hydroxylammonium synthesis zone.

According to the invention, the ratio $f_h/f_c<1.00$. Preferably, the ratio $f_h/f_c<0.99$, more preferably less than 0.98, in particular lower than 0.97. These decreased ratios result in a further decrease of the concentration of organic contaminants in the aqueous reaction medium exiting the cyclohexanone oxime synthesis. There is no specific lower limit for the ratio $f_h/f_c$. The ratio $f_h/f_c$ is generally higher than 0.5, preferably higher than 0.7, more preferably higher than 0.8.

In the cyclohexanone oxime synthesis zone, hydroxylammonium is reacted with cyclohexanone to form cyclohexanone oxime. Preferably, the aqueous reaction medium and a stream comprising the cyclohexanone and the organic solvent are contacted in countercurrent flow. This is a very effective way of separating cyclohexanone oxime from the aqueous reaction medium, A suitable process is for instance described in GB-A-1,138,750. Use may be made of known types of counterflow reactors, such as for instance pulsed columns filled with packing bodies or rotating disc reactors. It is also possible to use a system comprising a number, e.g. 3 to 6, of series-connected reactors equipped with stirrers, each of these reactors also being provided with a liquid-liquid separator. Preferably, the organic solvent has a solubility in water of less than 0.1% by weight at 20° C. Preferably, the organic solvent is selected from the group consisting of benzene, toluene, xylene, methylcyclopentane, cyclohexane and mixtures thereof. Most preferably, the organic solvent is toluene. Preferably, the cyclohexanone is dissolved in the organic solvent.

There is no specific lower limit for the concentration cyclohexanone oxime in the organic medium exiting the cyclohexanone oxime synthesis zone. Generally, the cyclohexanone oxime concentration in the organic medium exiting the cyclohexanone oxime synthesis zone is higher than 5 wt. %. An increased cyclohexanone oxime concentration in the organic medium exiting the cyclohexanone oxime synthesis zone has the advantage that separation of the organic solvent from the cyclohexanone oxime, for instance in a distillation process, can be carried out using less energy. Preferably, the cyclohexanone oxime concentration in the organic medium exiting the oxime synthesis zone is higher than 25 wt. %, more preferably higher than 30 wt. %, in particular higher than 35 wt. %, more in particular higher than 38 wt. %. An increased concentration cyclohexanone oxime may for instance be achieved by reducing the flow rate of the solvent into the oxime synthesis zone relative to the flow rate of the cyclohexanone into the oxime synthesis zone. Generally, the cyclohexanone oxime concentration in the organic medium exiting the cyclohexanone oxime synthesis zone, is lower than 95 wt. %, preferably lower than 80 wt. %, more preferably lower than 60 wt. %. All cyclohexanone oxime concentrations in the organic medium are given relative to the sum weight of the cyclohexanone oxime plus organic solvent.

Typically, the joint content of the cyclohexanone and cyclohexanone oxime in the aqueous reaction medium exiting the cyclohexanone oxime synthesis zone is below 0.2 wt. % (2000 ppm), preferably below 0.1 wt. %, more preferably below 0.05 wt. %, in particular below 0.02 wt. %, more in particular below 0.01 wt. %, most preferably below 0.005 wt. % (relative to the weight of the aqueous reaction medium).

We have found that an increase of the concentration cyclohexanone oxime in the organic medium exiting the cyclohexanone oxime synthesis zone may result in an increase of the concentration of organic contaminants in the aqueous reaction medium exiting the hydroxylammonium synthesis zone. The process according to the invention has the advantage that this effect is mitigated or avoided.

The cyclohexanone oxime synthesis zone may be operated at a temperature ranging from 40 to 150° C. and at atmospheric, sub-atmospheric, or elevated pressures, preferably between 0.05 and 0.5 MPa, more preferably between 0.1 and 0.2 MPa, most preferably between 0.1 and 0.15 MPa. Preferably, the aqueous reaction medium entering the cyclohexanone oxime synthesis zone has a pH of between 1 and 6, more preferably between 1.5 and 4.

There is no specific lower limit for the concentration hydroxylammonium in the aqueous reaction medium entering the cyclohexanone oxime synthesis zone. Generally, the concentration hydroxylammonium in the aqueous reaction medium entering the cyclohexanone oxime synthesis zone is higher than 0.7 mol/l. An increased concentration of hydroxylammonium is advantageous, since the conversion of hydroxylammonium in the cyclohexanone oxime synthesis zone may then be increased. Furthermore, the amount of cyclohexanone oxime produced per unit of time can be increased by increasing the concentration hydroxylammonium in the aqueous reaction medium entering the cyclohexanone oxime synthesis zone. Preferably, the concentration hydroxylammonium in the aqueous reaction medium entering the cyclohexanone oxime synthesis zone is higher than 0.8 mol/l, more preferably higher than 1.0 mol/l, in particular higher than 1.2 mol/l, more in particular higher than 1.4 mol/l, most preferably higher than 1.6 mol/l. An increased concentration hydroxylammonium in the aqueous reaction medium entering the cyclohexanone oxime synthesis zone may for instance be achieved by increasing the residence time in the hydroxylammonium synthesis zone and/or by increasing the nitrate concentration in the aqueous reaction medium entering the hydroxylammonium synthesis zone. There is no specific upper limit for the concentration hydroxylammonium in the aqueous reaction medium entering the cyclohexanone oxime synthesis zone. Generally, the concentration hydroxylammonium in the aqueous reaction medium entering the cyclohexanone oxime synthesis zone is below 2.5 mol/l.

We have found that an increase of the concentration hydroxylammonium in the aqueous reaction medium entering the cyclohexanone oxime systhesis zone may result in an increase of the concentration of organic contaminants in the aqueous reaction medium exiting the cyclohexanone oxime synthesis zone. The process according to the invention has the advantage that this effect is mitigated or avoided.

The aqueous reaction medium contains phospate. Generally, the phosphate concentration in the aqueous reaction medium entering the cyclohexanone oxime synthesis zone is higher than 2.0 mol/l, preferably higher than 2.5 mol/l, more preferably higher than 3.0 mol/l, in particular higher than 3.3 mol/l, more in particular higher than 3.5 mol/l, most preferably higher than 3.7 mol/l. We have found that increasing the phosphate concentration in the aqueous reaction medium entering the cyclohexanone oxime synthesis zone is advantageous since it results in a decrease of the concentration of organic contaminants in the aqueous reaction medium exiting the cyclohexanone oxime synthesis zone. Preferably, the phosphate concentration is chosen such that no crystallization occurs, which depends, inter alia, on the temperature and the concentration of other components in the aqueous reaction medium. Generally, the phosphate concentration in the aqueous reaction medium entering the cyclohexanone oxime synthesis zone is lower than 8 mol/l, preferably lower than 5 mol/l, more preferably lower than 4.5 mol/l. As used herein, the phosphate concentration denotes the sum concentration of all phosphates, irrespective of the form in which they are present, expressed in mol per liter of aqueous reaction reaction medium. Preferably, the phosphates are present as $PO_4^{3-}$, $HPO_4^{2-}$, $H_2PO_4^-$, $H_3PO_4$, salts of $PO_4^{3-}$, $HPO_4^{2-}$, $H_2PO_4^-$, and/or combinations thereof.

In a preferred embodiment, the cyclohexanone oxime synthesis zone comprises a reaction zone in which hydroxylammonium is reacted with cyclohexanone to form cyclohexanone oxime by contacting the aqueous reaction medium and the stream comprising the cyclohexanone and the organic solvent in countercurrent flow, and an extraction zone in which the aqueous reaction medium and an organic solvent are contacted, preferably in countercurrent flow, the aqueous reaction medium entering the cyclohexanone oxime synthesis zone being fed to the reaction zone, the aqueous reaction medium exiting the reaction zone being fed to the extraction zone. This embodiment has the advantage that organic residuals, in particular cyclohexanone and cyclohexanone oxime, are separated from the aqueous reaction medium exiting the reaction zone. Preferably, cyclohexanone is fed to the oxime synthesis zone between the reaction zone and the extraction zone. Preferably, organic solvent exiting the extraction zone is fed to the reaction zone. Preferably, cyclohexanone is fed to the cyclohexanone oxime synthesis zone in the organic solvent entering the extraction zone. Use may be made of known types of extractors such as for instance an extraction column, or one or more reactors equipped with stirrers, optionally series-connected, each of these reactors also being provided with a liquid-liquid separator. Preferably, a pulsed column filled with packing bodies is used. The reaction zone and extraction zone are preferably operated at a temperature ranging from 40 to 150° C. and at atmospheric, subatmospheric, or elevated pressures, preferably between 0.05 and 0.5 MPa, more preferably between 0.1 and 0.2 MPa, most preferably between 0.1 and 0.15 MPa. Use may be made of known types of extractors such as for instance extraction columns, preferably, pulsed columns filled with packing bodies, or one or more reactors equipped with stirrers, optionally series-connected, each of these reactors also being provided with a liquid-liquid separator. Preferably, the organic solvent has a solubility in water of less than 0.1% by weight at 20° C. Preferably, the organic solvent is selected from the group consisting of benzene, toluene, xylene, methylcyclopentane, cyclohexane and mixtures thereof. Most preferably, the organic solvent is toluene. The operating conditions for the reaction zone and the extraction zone are not necessarily the same. Preferably, the same solvent is used in the reaction zone and the extraction zone. Preferably, the joint content of the cyclohexanone and cyclohexanone oxime in the aqueous reaction medium exiting the extraction zone is below 0.2 wt. % (2000 ppm), more preferably below 0.05 wt. %, in particular below 0.02 wt. %, more in particular below 0.01 wt. %, most preferably below 0.005 wt. % (relative to the weight of the aqueous reaction medium).

Preferably, the aqueous reaction medium exiting the cyclohexanone oxime synthesis zone or exiting the extraction zone is subjected to stripping to achieve further reduction in organic contaminants. The stripping process described in U.S. Pat. No. 3,940,442 may for instance be used. It is preferred that the joint content of cyclohexanone and cyclohexanone in the aqueous reaction medium entering the hydroxylammonium synthesis zone is not more than 0.02 wt. % (200 ppm), more preferably not more than 0.005 wt. %, in particular not more than 0.002 wt. %, more in particular not more than 0.001 wt. % and most preferably not more than 0.0002 wt. % (relative to the weight of the aqueous reaction medium).

Generally, the aqueous reaction medium is an acidic, buffered reaction medium. The aqueous reaction medium may contain ammonium ($NH_4^+$), for instance formed as a by-product in the synthesis of hydroxylammonium. Preferably, in the aqueous reaction medium entering the cyclohexanone oxime synthesis zone, the ratio $c(NH_4^+)/c(phosphate)$ is between 0.1 and 3, more preferably between 0.2 and 2, most preferably between 0.5 and 1.5, wherein $c(NH_4^+)$ represents the concentration of $NH_4^+$ in mol/l and c(phosphate) represents the phosphate concentration in mol/l.

Generally, the aqueous reaction medium entering the cyclohexanone oxime synthesis zone contains nitrate ($NO_3^-$). Preferably, in the aqueous reaction medium entering the cyclohexanone oxime synthesis zone, the $c(NO_3^-)/c$(phosphate) is between 0.05 and 1, more preferably between 0.1 and 0.5, wherein $c(NO_3^-)$ represents the concentration of $NO_3^-$ in mol/l and c(phosphate) represents the phosphate concentration in mol/l.

In the hydroxylammonium synthesis zone hydroxylammonium is formed by catalytic reduction of nitrate with hydrogen. The hydroxylammonium synthesis zone may be operated at a temperature ranging from 20 to 100° C., preferably 30–90° C., more preferably 40–65° C., and at atmospheric, sub-atmospheric or elevated pressures, preferably between 0.1 and 5 MPa, more preferably between 0.3 and 3 MPa, and in particular between 0.5 and 2 MPa (hydrogen partial pressure). Preferably, the pH in the hydroxylammonium synthesis zone is between 0.5 and 6, more preferably between 1 and 4. The catalyst employed in this zone is generally present in a range of between 1 to 25 wt. %, preferably between 5 to 15 wt. % of a precious metal, relative to total weight of support plus catalyst. Preferably, the catalyst is a palladium containing catalyst, for instance a palladium or a palladium-platinum catalyst, present on a support, such as for instance carbon or alumina support. Generally, the catalyst is present in the hydroxylammonium synthesis zone in an amount of 0.2–5 wt. % relative to the total liquid weight in the hydroxylammonium reactor vessel(s).

DESCRIPTION OF AN EMBODIMENT

Figure 1:
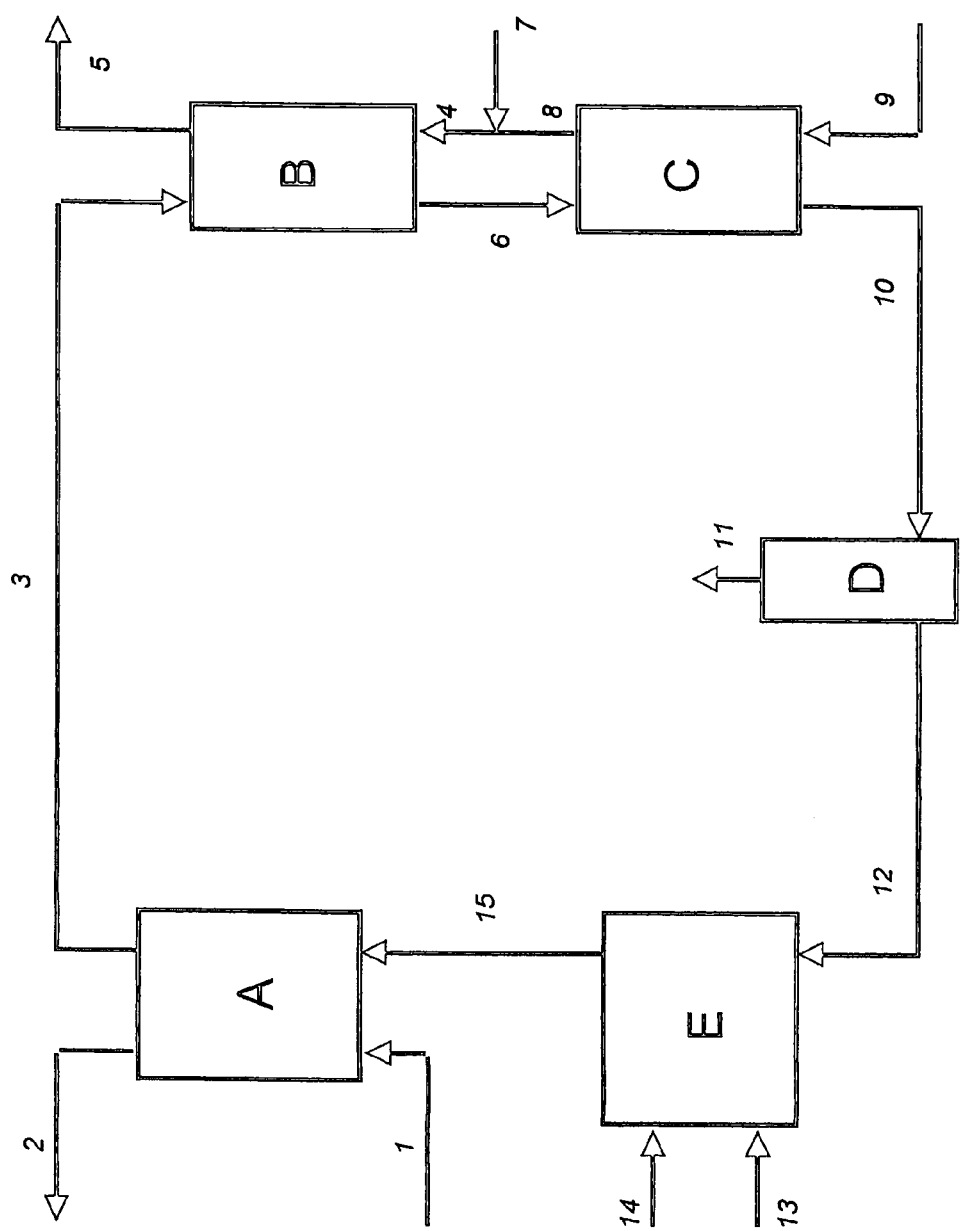
FIG. 1 is a schematic diagram of an embodiment of the process according to the present invention.

Referring to FIG. 1, A represents the hydroxylammonium synthesis zone. A cyclohexanone oxime synthesis zone is used comprising reaction zone B and extraction zone C. To zone A, containing catalyst, hydrogen is fed via line 1; unreacted hydrogen is discharged, with any other gases, via line 2. The aqueous reaction medium, containing, inter alia, phosphate, is fed to zone A through line 15 and after having been enriched in hydroxylammonium (also ammonium as a by-product) in the hydroxylammonium synthesis zone, is passed to the reaction zone B via line 3. The cyclohexanone to be converted is fed in an organic solvent to the reaction zone B via line 4. The cyclohexanone is introduced into the organic solvent via line 7. The ratio $f_h/f_c$ is less than 1.00. The largest part of cyclohexanone oxime produced and dissolved in the organic solvent is removed from the system via line 5.

Upon exiting reaction zone B, the aqueous reaction medium is passed to extraction zone C via line 6. Upon exiting reaction zone B, the hydroxylammonium content of the aqueous reaction medium has been reduced by reaction and contains small quantities of cyclohexanone and cyclohexanone oxime contaminants. The organic solvent enters extraction zone C through line 9. Within extraction zone C, additional cyclohexanone oxime is removed from the aqueous reaction medium and carried out of zone C in the organic solvent through line 8. In the extraction zone C, the residual organic contaminants (cyclohexanone+cyclohexanone oxime) in the aqeuous reaction medium is reduced.

The aqueous reaction medium exits extraction zone C through line 10 which passes the aqueous reaction medium to a separation operation, stripping column D. In this column, cyclohexanone oxime is hydrolyzed to cyclohexanone and the cyclohexanone thus formed together with the cyclohexanone already present is discharged with other organic materials and water (e.g., as an azeotrope) through line 11. The aqueous reaction medium being recycled in the system then passes through line 12 to zone E. In zone E, nitric acid is produced. Preferably, nitric acid is produced, at zone E or thereafter, by reacting air fed through line 13 with ammonia fed through line 14 and with water from the aqueous reaction medium. Directly supplying nitric acid to the aqueous reaction medium instead of producing nitric acid is also possible. Accordingly, the nitrate level is increased in the inorganic medium in zone E. In zone E, ammonium ions, e.g. formed as a by-product in the synthesis of hydroxylammonium, may be converted by means of gases containing nitrogen oxides. However, other methods for removal of ammonium ions may also be used. The aqueous reaction medium then completes the cycle by returning to hydroxylammonium synthesis zone A via line 15. The process is carded out continuously.

The following specific examples are to be construed as merely illustrative, and not limitive, of the remainder of the disclosure.

EXAMPLES AND COMPARATIVE EXPERIMENTS

Example 1

Cyclohexanone oxime was produced using the set-up as shown in FIG. 1.

In hydroxylammonium synthesis zone A (containing a catalyst (10 wt. % Pd supported on carbon), operated at a temperature of 52° C. at a pressure of 1 MPa (hydrogen partial pressure)) an aqueous reaction medium was produced per unit of time having the following composition:
1.28 mol $NH_3OH.H_2PO_4$
1.33 mol $NH_4H_2PO_4$
0.70 mol $H_3PO_4$
1.86 mol $NH_4NO_3$
39.6 mol $H_2O$ and fed (via line 3) to reaction zone B (a pulsed packed column, operated at 55° C.). Per unit of time 1.32 mol cyclohexanone was fed (via line 7) to zone B, resulting in a ratio $f_h/f_c$ of 0.97. Per unit of time 1.25 mol cyclohexanone oxime (141.3 g) was formed. Per unit of time 251 g toluene was fed to extraction zone C, the cyclohexanone oxime concentration in the organic medium (relative to the sum weight of toluene plus cyclohexanone oxime) leaving zone B via line 5 being 36 wt. %. The aqueous reaction medium exiting zone B was fed to extraction zone C (a pulsed packed column, operated at 70° C.). The resulting concentration organic residuals (cyclohexanone+cyclohexanone oxime) in the aqueous reaction medium exiting extraction zone C was 6 ppm (0.0006 wt. %).

Comparative Experiment A

Example 1 was repeated. However, per unit of time 1.24 mol cyclohexanone was fed to zone B, i.e. the ratio $f_h/f_c$ was 1.03 instead of 0.97. The flow rate of the toluene was adjusted such that the cyclohexanone oxime concentration in the organic medium (relative to the sum weight of toluene plus cyclohexanone oxime) was kept 36 wt. %. The resulting concentration organic residuals (cyclohexanone+cyclohexanone oxime) in the aqueous medium exiting extraction zone C was 21 ppm (0.0021 wt. %). When comparing example 1 and comparative experiment A, it is shown that an decrease of the ratio $f_h/f_c$ to below 1.00 according to the invention results in a decrease of the concentration organic residuals (cyclohexanone+cyclohexanone oxime).

Comparative Experiment B

Comparative experiment A was repeated. However, the flow rate of the toluene was decreased such that the concentration cyclohexanone oxime dissolved in toluene withdrawn from zone B, was 42 wt. % (relative to the sum weight of cyclohexanone plus cyclohexanone oxime). The resulting concentration organic residuals (cyclohexanone+cyclohexanone oxime) in the aqueous medium exiting extraction zone C was 356 ppm (0.0356 wt. %).

Example 2

Comparative experiment B was repeated. However, per unit of time 1.32 mol cyclohexanone was fed to zone B, resulting in a ratio $f_h/f_c$ of 0.97 instead of 1.03. The resulting concentration organic residuals (cyclohexanone+cyclohexanone oxime) in the aqueous medium exiting extraction zone C was 96 ppm (0.0096 wt. %). When comparing example 2 and comparative experiment B, it is shown that a decrease of the ratio $f_h/f_c$ to below 1.00 according to the invention results in a decrease of the concentration organic residuals (cyclohexanone+cyclohexanone oxime).

Particular embodiments of this invention have been illustrated and described above. However, those of ordinary skill in the art understand that various modifications can be made, without departing from the spirit and scope of the invention. Accordingly, interpretation of this invention should not be limited, except as by the appended claims.

What is claimed is:

1. Process for the production of cyclohexanone oxime in which a phosphate-containing aqueous reaction medium is cycled from a hydroxylammonium synthesis zone (A) to a cyclohexanone oxime synthesis zone and back to the hydroxylammonium synthesis zone (A), in which hydroxylammonium synthesis zone hydroxylammonium is formed by catalytic reduction of nitrate with hydrogen, which cyclohexanone oxime synthesis zone comprises a reaction zone (B) and an extraction zone (C), said process comprising;
(i) feeding the aqueous reaction medium to reaction zone (B), and from reaction zone (B) to extraction zone (C);
(ii) feeding cyclohexanone and an organic solvent into the cyclohexanone oxime synthesis zone, cyclohexanone being fed to the cyclohexanone oxime synthesis zone between the reaction zone (B) and the extraction zone (C);
(iii) in said reaction zone (B), reacting hydroxylammonium with cyclohexanone to form cyclohexanone oxime by contacting the aqueous reaction medium with a stream containing the cyclohexanone and the organic solvent;
(iv) in said extraction zone (C), contacting the aqueous reaction medium and the organic solvent;
(v) withdrawing an organic medium comprising the organic solvent and cyclohexanone oxime from the cycrohexanone oxime synthesis zone; and wherein the ratio $f_h/f_c<1.00$, wherein $f_h$ represents the molar quantity of hydroxylammonium fed to the cyclohexanone oxime synthesis zone per unit of time (in mol/s), and $f_c$ represents the molar quantity of cyclohexanone fed to the cyclohexanone oxime synthesis zone per unit of time (in mol/s).

2. Process for the production of cyclohexanone oxime in a cyclohexanone oxime synthesis zone, said cyclohexanone oxime synthesis zone comprising a reaction zone (B) and an extraction zone (C), said process comprising:
(i) feeding an aqueous reaction medium containing hydroxylammonium, phosphate and nitrate to reaction zone (B), and from reaction zone (B) to extraction zone (C)
(ii) feeding cyclohexanone and an organic solvent into a cyclohexanone oxime synthesis zone, cyclohexanone being fed to the cyclohexanone oxime synthesis zone between the reaction zone (B) and the extraction zone (C);
(iii) in said reaction zone (B), reacting hydroxylammonium with cyclohexanone to form cyclohexanone oxime by contacting the aqueous reaction medium with a stream containing the cyclohexanone and the organic solvent;
(iv) in said extraction zone (C), contacting the aqueous reaction medium and the organic solvent;
(v) withdrawing an organic medium comprising the organic solvent and cyclohexanone oxime from the cyclohexanone oxime synthesis zone, wherein the ratio $f_h/f_c<1.00$, wherein $f_h$ represents the molar quantity of hydroxylammonium fed to the cyclohexanone oxime synthesis zone per unit of time (in mol/s)

$f_c$ represents the molar quantity of cyclohexanone fed to the cyclohexanone oxime synthesis zone per unit of time (in mol/s).

3. Process according to claim 1, wherein the ratio $f_h/f_c<0.99$.

4. Process according to claim 3, wherein the ratio $f_h/f_c<0.98$.

5. Process according to claim 1, wherein the cyclohexanone oxime concentration in the organic medium exiting the cyclohexanone oxime synthesis zone is higher than 25 wt. %.

6. Process according to claim 5, wherein the cyclohexanone oxime concentration in the organic medium exiting the cyclohexanone oxime synthesis zone is higher than 30 wt. %.

7. Process according to claim 6, wherein the cyclohexanone oxime concentration in the organic medium exiting the cyclohexanone oxime synthesis zone is higher than 35 wt. %.

8. Process according to claim 1, wherein the concentration of hydroxylammonium in the aqueous reaction medium entering the cyclohexanone oxime synthesis zone is higher than 0.7 mol/l.

9. Process according to claim 8, wherein the concentration of hydroxylammonium in the aqueous reaction medium entering the cyclohexanone oxime synthesis zone is higher than 1.0 mol/l.

10. Process according to claim 1, wherein the aqueous reaction medium and a stream comprising the cyclohexanone and the organic solvent are contacted in countercurrent flow.

11. Process according to claim 1, wherein the organic solvent is selected from the group consisting of benzene, toluene, xylene, methylcyclopentane, cyclohexane, and mixtures thereof.

12. Process according to claim 1, wherein the phosphate concentration in the aqueous reaction medium entering the cyclohexanone oxime synthesis zone is higher than 2.0 mol/l.

13. Process according to claim 1, wherein the joint content of cyclohexanone and cyclohexanone oxime in the aqueous reaction medium exiting the cyclohexanone oxime synthesis zone is below 0.2 wt. %.

* * * * *